United States Patent
Kreilgård et al.

(12)

(10) Patent No.: US 6,770,295 B1
(45) Date of Patent: Aug. 3, 2004

(54) THERAPEUTIC FORMULATION FOR ADMINISTERING TOLTERODINE WITH CONTROLLED RELEASE

(75) Inventors: Bo Kreilgård, Hillerød (DK); Lene Orup Jacobsen, Gentofte (DK); Ulla Hoeck, Hillerød (DK); Helle Kristensen, Slangerup (DK); Torkel Gren, Uppsala (SE); Lisbeth Nilvebrant, Bromma (SE); Anders Ringberg, Stockholm (SE); Martin Wikberg, Kullavik (SE); Bengt Hallén, Sollentuna (SE); Birgitta Olsson, Stenhamra (SE); Jan Strömbom, Vattholma (SE)

(73) Assignee: Pharmacia AB, Stockholm (SE)

( * ) Notice: Subject to any disclaimer, the term of this patent is extended or adjusted under 35 U.S.C. 154(b) by 0 days.

(21) Appl. No.: 09/582,498

(22) PCT Filed: Aug. 26, 1999

(86) PCT No.: PCT/SE99/01463

§ 371 (c)(1),
(2), (4) Date: Nov. 14, 2000

(87) PCT Pub. No.: WO00/12069

PCT Pub. Date: Mar. 9, 2000

(30) Foreign Application Priority Data

Aug. 27, 1998 (SE) .............................................. 9802864
Nov. 11, 1998 (SE) .............................................. 9803871

(51) Int. Cl.$^7$ .............................. A61K 9/22; A61K 9/52; A61K 9/70; A61F 13/00
(52) U.S. Cl. ...................... 424/457; 424/468; 424/449
(58) Field of Search .................. 424/449, 457, 424/468, 458, 459, 461, 462

(56) References Cited

U.S. PATENT DOCUMENTS 3,598,123 A * 8/1971 Zaffaroni ..................... 128/268
4,008,719 A * 2/1977 Theeuwes et al. .......... 128/260

FOREIGN PATENT DOCUMENTS

| WO | WO9323025 | 11/1993 |
| WO | WO9612477 | 5/1996 |
| WO | WO9803067 | 1/1998 |
| WO | WO9811888 | 3/1998 |

OTHER PUBLICATIONS

Nilvebrant, L. et al., Euro. J. of Pharmacol., vol. 327 (1997) pp. 195–207.
Nilvebrant, L. et al., Life Sci., vol. 60, Nos. 13/14 (1997) pp. 1129–1136.
Brynne, N. et al., Intl. J. of Clin. Pharmacol. and Thera., vol. 35, No. 7 (1997) pp. 287–295.
Stahl, M.M.S., Neurology and Urodynamics, vol. 14 (1995) pp. 647–655.
Nilsson, C.G. et al., Neurology and Urodynamics, vol. 16 (1997) pp. 533–542.

* cited by examiner

Primary Examiner—James M. Spear
(74) Attorney, Agent, or Firm—Craig M. Bell

(57) ABSTRACT

The present invention is drawn to a method of treating an unstable or overactive urinary bladder by treating the patient with tolterodine or a tolterodine-related compound, or pharmaceutically acceptable salt thereof, with a controlled release formulation that maintains a substantially constant serum level of the active moiety or moieties for at least 24 hours. The present invention is further drawn to a formulation for the method.

27 Claims, 2 Drawing Sheets

THERAPEUTIC FORMULATION FOR ADMINISTERING TOLTERODINE WITH CONTROLLED RELEASE

This application is the national phase under 35 U.S.C. §371 of PCT International Application No. PCT/SE99/01463 which has an International filing date of Aug. 26, 1999, which designated the United States of America.

The present invention relates to an improved method of treating unstable or overactive urinary bladder as well as a formulation therefor.

A substantial part (5–10%) of the adult population suffers from urinary incontinence, and the prevalence, particularly of so-called urge incontinence, increases with age. The symptoms of an unstable or overactive bladder comprise urge incontinence, urgency and urinary frequency. It is assumed that unstable or overactive bladder is caused by uncontrolled contractions of the bundles of smooth muscle fibres forming the muscular coat of the urinary bladder (the detrusor muscle) during the filling phase of the bladder. These contractions are mainly controlled by cholinergic muscarinic receptors, and the pharmacological treatment of unstable or overactive bladder has been based on muscarinic receptor antagonists. The drug of choice has for a long time been oxybutynin.

Oxybutynin, which chemically is the DL-racemic form of 4-diethylamino-2-butynyl-phenylcyclohexylglycolate, is given orally, usually as a tablet or syrup. Oxybutynin, usually administered as the chloride salt, is metabolized to an active metabolite, N-desethyl-oxybutynin. The drug is rapidly absorbed from the gastrointestinal tract following administration and has a duration of from three to six hours. While the effectiveness of oxybutynin has been well documented, its usefulness is limited by classical antimuscarinic side-effects, particularly dry mouth, which often leads to discontinuation of treatment.

WO 96/12477 discloses a controlled release delivery system for oxybutynin, which delivery system is said not only to be of convenience to the patient by reducing the administration to a once daily regimen, but also to reduce adverse side-effects by limiting the initial peak concentrations of oxybutynin and active metabolite in the blood of the patient.

The alleged relief of side-effects by reducing or eliminating peak concentrations through administration of the controlled release delivery system is, however, contradicted by a later published clinical report, Nilsson, C. G., et al., Neurourology and Urodynamics 16 (1997) 533–542, which describes clinical tests performed with the controlled release delivery system disclosed in WO 96/12477 above. In the clinical tests reported, a 10 mg controlled release oxybutynin tablet was compared with the administration of a conventional (immediate release) 5 mg tablet given twice daily to urge incontinent patients. While high peak levels of the drug obviously were eliminated with the controlled release oxybutynin tablet, no difference in side-effects between the controlled release tablet and the conventional tablet was observed. The advantage of the controlled release tablet thus resided merely in enhancing treatment compliance by its once-a-day dosage rather than also reducing side-effects as stated in WO 96/12477.

Recently, an improved muscarinic receptor antagonist, tolterodine, (R)-N,N-diisopropyl-3-(2-hydroxy-5-methylphenyl)-3-phenylpropanamine, has been marketed for the treatment of urge incontinence and other symptoms of unstable or overactive urinary bladder. Both tolterodine and its major, active metabolite, the 5-hydroxymethyl derivative of tolterodine, which significantly contributes to the therapeutic effect, have considerably less side-effects than oxybutynin, especially regarding the propensity to cause dry mouth. While tolterodine is equipotent with oxybutynin in the bladder, its affinity for muscarinic receptors of the salivary gland is eight times lower than that of oxybutynin; see, for example, Nilvebrant, L., et al., European Journal of Pharmacology 327 (1997) 195–207. The selective effect of tolterodine in humans is described in Stahl, M. M. S., et al., Neurourology and Urodynamics 14 (1995) 647–655, and Bryne, N., International Journal of Clinical Pharmacology and Therapeutics, Vol. 35, No. 7 (1995) 287–295.

The currently marketed administration form of tolterodine is filmcoated tablets containing 1 mg or 2 mg of tolterodine L-tartrate for immediate release in the gastrointestinal tract, the recommended dosage usually being 2 mg twice a day. While, as mentioned, the side-effects, such as dry mouth, are much lower than for oxybutynin, they still exist, especially at higher dosages.

According to the present invention it has now surprisingly been found that, contrary to the case of oxybutynin, the substantial elimination of peak serum levels of tolterodine and its active metabolite through controlled release of tolterodine for an extended period of time, such as through a once-daily administration form, while maintaining the desired effect on the bladder, indeed gives a significant reduction of the (already low) side-effects, particularly dry mouth, compared with those obtained for the same total dosage of immediate release tablets over the same period. In other words, eliminating the peak serum levels of the active moiety affects the adverse effects, and particularly dry mouth, more than the desired effect on the detrusor activity, simultaneously as the flattening of the serum concentration does not lead to loss of activity or increased incidence of urinary retention or other safety concerns. Thus, in addition to the convenience advantage of controlled release administration, one may either (i) for a given total dosage of tolterodine, reduce the side-effects, such as dry mouth, or (ii) for a given level of acceptable side-effects, increase the dosage of tolterodine to obtain an increased effect on the bladder, if desired.

In one aspect, the present invention therefore provides a method of treating unstable or overactive urinary bladder, which method comprises administering to a (mammal) patient in need of such treatment tolterodine or a tolterodine-related compound, or a pharmaceutically acceptable salt thereof, through a controlled release formulation that administers tolterodine or said tolterodine-related compound, or salt thereof, at a controlled rate for at least 24 hours. It is preferred that the dosage form formulation is capable of maintaining a substantially constant serum level of the active moiety or moieties for said at least 24 hours.

Overactive urinary bladder encompasses detrusor instability, detrusor hyperreflexia, urge incontinence, urgency and urinary frequency.

As mentioned above, the chemical name of tolterodine is (R)-N,N-diisopropyl-3-(2-hydroxy-5-methylphenyl)-3-phenylpropanamine. The term "tolterodine-related compound" is meant to encompass the major, active metabolite of tolterodine, i.e. (R)-N,N-diisopropyl-3-(2-hydroxy-5-hydroxymethylphenyl)-3-phenylpropanamine; the corresponding (S)-enantiomer to tolterodine, i.e. (S)-N,N-diisopropyl-3-(2-hydroxy-5-methylphenyl)-3-phenylpropanamine; the 5-hydroxymethyl metabolite of the (S)-enantiomer, i.e. (S)-N,N-diisopropyl-3-(2-hydroxy-5-hydroxymethylphenyl)-3-phenylpropanamine; as well as the corresponding racemate to tolterodine, i.e. (R,S)-N,N-diisopropyl-3-(2-hydroxy-5-methylphenyl)-3-phenylpropanamine; and prodrug forms thereof.

By the term "active moiety or moities" is meant the sum of free or unbound (i.e. not protein bound) concentrations of (i) tolterodine and active metabolite thereof, when tolterodine (or prodrug form) is administered; or (ii) tolterodine and active metabolite thereof and/or (S)-enantiomer to tolterodine and active metabolite thereof, when the corresponding racemate (or prodrug form) is administered; or (iii) active metabolite, when the (R)-5-hydroxymethyl metabolite of tolterodine (or prodrug form) is administered; or (iv) (S)-enantiomer to tolterodine and active metabolite thereof, when the (S)-enantiomer (or prodrug) is administered; or (v) active (S)-metabolite, when the (S)-5-hydroxymethyl metabolite is administered.

The term "substantially constant" with respect to the serum level of active moiety or moieties means that the release profile of the controlled release formulation should essentially not exhibit any peak values. This may, more sophistically, also be expressed by reference to the "flucuation index" (FI) for the serum concentration of (unbound) active moiety (or sum of active moities when relevant), where the fluctuation index FI is calculated as $$FI=(Cmax-Cmin)/AUC\tau/\tau$$

wherein Cmax and Cmin are the maximum and minimum concentrations, respectively, of active moiety, $AUC\tau$ is the area under the serum concentration profile (concentration vs time curve) for dosage interval $\tau$, and $\tau$ is the length of the dosage interval. Thus, according to the present invention, the controlled release formulation should provide a mean fluctuation index (for n being at least 30) that is usually not higher than about 2.0, more preferably not higher than about 1.5, particularly not higher than about 1.0, for example not higher than about 0.8.

For tolterodine and its 5-hydroxymethyl metabolite, the 24-hour exposure, expressed as AUC unbound active moiety (tolterodine plus metabolite) is usually in the range of from about 5 to about 150 nM*h, preferably from about 10 to about 120 nM*h, depending on the dosage needed by the particular patient. The indicated limits are based upon calculation of the unbound concentrations of active moiety assuming a fraction unbound of 3.7% for tolterodine and 36% for the 5-hydroxymethyl metabolite (Nilvebrant, L., et al., Life Sciences, Vol. 60, Nos. 13/14 (1997) 1129–1136).

Correspondingly, for tolterodine and its 5-hydroxymethyl metabolite, the average (blood) serum or plasma levels are usually in the range of about 0.2 to about 6.3 nM, preferably in the range of about 0.4 to about 5.0 nM.

Tolterodine, its corresponding (S)-enantiomer and racemate and the preparation thereof are described in e.g. WO 89/06644. For a description of the active (R)-5-hydroxymethyl metabolite of tolterodine (as well as the (S)-5-hydroxymethyl metabolite), it may be referred to WO 94/11337. The (S)-enantiomer and its use in the treatment of urinary and gastrointestinal disorders is described in WO 98/03067.

In another aspect, the present invention provides a pharmaceutical formulation containing tolterodine or a tolterodine-related compound, or a pharmaceutically acceptable salt thereof, which formulation when administered to a patient provides controlled release of tolterodine or said tolterodine-related compound, or salt thereof, for at least 24 hours, preferably such that a substantially constant serum level of the active moiety or moieties is maintained for said at least 24 hours.

Still another aspect of the present invention provides the use of tolterodine or a tolterodine-related compound, or a pharmaceutically acceptable salt thereof, for the manufacture of a therapeutical formulation for treating unstable or overactive urinary bladder, which formulation provides a controlled release of tolterodine or said tolterodine-related compound, or salt thereof at a controlled rate for at least 24 hours, preferably such that a substantially constant serum level of the active moiety or moieties is maintained for said at least 24 hours.

The controlled release formulation is preferably an oral delivery system or a transdermal preparation, such as a transdermal patch, but also other controlled release forms may, of course, be contemplated, such as buccal tablets, rectal suppositories, subcutaneous implants, formulations for intramuscular administration.

An exemplary type of oral controlled release formulation, a specific embodiment of which is described in Example 1 below, is a multi-unit formulation comprising controlled-release beads. Each bead comprises (i) a core unit of a water-soluble, water-swellable or water-insoluble inert material (having a size of about 0.05 to 2 about 2 mm), such as e.g. a sucrose sphere; (ii) a first layer on the core of a substantially water-insoluble (often hydrophilic) polymer (this layer may be omitted in the case of an insoluble core, such as e.g. of silicon dioxide), (iii) a second layer of a water-soluble polymer having an active ingredient dissolved or dispersed therein, and (iv) a third polymer layer effective for controlled release of the active ingredient (e.g. a water-insoluble polymer in combination with a water-soluble polymer) In the case of an oral controlled release formulation for once-daily administration, the dosage of tolterodine (or tolterodine related compound) is, for example, 4 mg or 6 mg.

A transdermal patch for tolterodine or tolterodine-related compound is described in our co-pending international application "Transdermally administered tolterodine as antimuscarinic agent for the treatment of overactive bladder" (based on Swedish patent application no. 9802864-0, filed on Aug. 27, 1998), the full disclosure of which is incorporated by reference herein. Illustrative patch formulations are described in Example 2 below.

With the guidance of the disclosure herein, the skilled person may either adapt controlled release administration forms, such as tablets, capsules, patches etc, known in the art, to obtain the objectives of the present invention, or design modified or new controlled release administration forms.

The invention is illustrated by the following Examples, without, however, limiting the scope of the invention in any way. Percentages are by weight, unless otherwise stated. Reference will be made to the accompnaying drawings, in which:

EXAMPLE 1

TOLTERODINE ORAL CR CAPSULE AND IR TABLET

Figure 1:
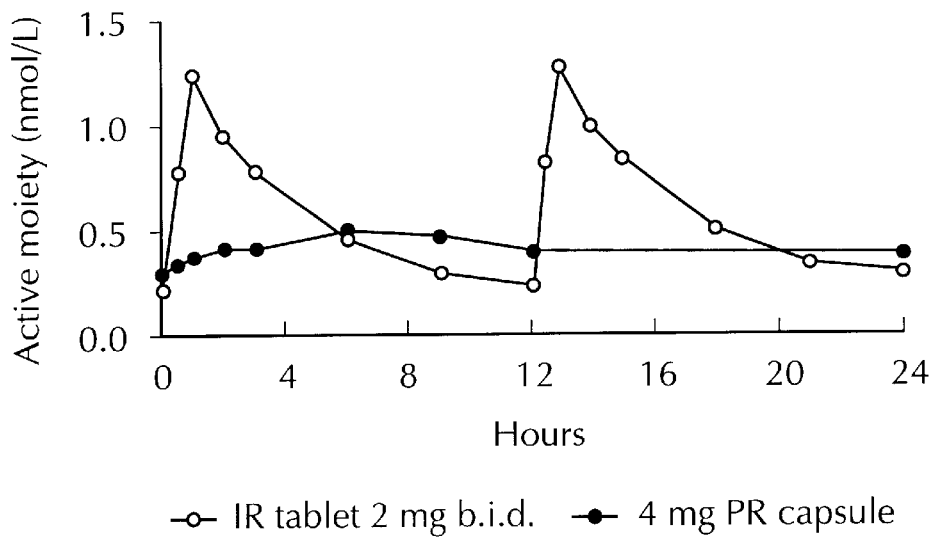
FIG. 1 is a diagram showing the variation of serum concentration (nmol/L) of (unbound) active moiety with time (hours) during 24 hours when administering a predetermined total dosage of tolterodine (4 mg) through (i) an immediate release tablet (2 mg) twice daily as in the prior art, and (ii) a controlled release capsule (4 mg) once daily in accordance with the present invention.

Preparation of Tolterodine CR Capsules 2 mg and 4 mg

A controlled release (CR) capsule containing non-pareil beads coated by (i) an ethylcellulose layer, (ii) a tolterodine/

HPMC layer, and (iii) a sustained release ethylcellulose/HPMC layer was prepared as follows:

1200 g of (starch-containing) sugar spheres, 20–25 mesh, were charged into a Wurster fluid bed and sequentially coated with the following three coating solutions:

(1) a Surelease® sealcoating solution prepared by mixing 788 g of Sureleasee with 563 g of purified water (Surelease® is an aqueous filmcoating dispersion, about 25% solids, consisting primarily of ethylcellulose plasticized with fractionated coconut oil; manufactured by Colorcon, Inc., West Point, Pa., U.S.A.);

(2) a suspension prepared by first dissolving 35.0 g of tolterodine L-tartrate in 2190 g of purified water, and then mixing the solution with 6.6 g of Hypromellose, 5 cP (hydroxypropylmethyl cellulose (HPMC)); and (3) a sustained release coating solution prepared by mixing 29 g of Hypromellose, 5 cP, with 375 g of purified water, and then mixing with 695 g of Surelease®.

After drying, the coated spheres were filled into hard gelatin capsule shells (size 3, white/white) to obtain 2 mg and 4 mg capsules, respectively, of the composition (filling mass for 2 mg capsule, 169–207 mg/capsule):

|  | 2 mg capsule | 4 mg capsule |
| --- | --- | --- |
| Tolterodine L-tartrate | 2.0 mg | 4.0 mg |
| sugar spheres, 20–25 mesh | 69 mg | 137 mg |
| Surelease ® | 21 mg | 42 mg |
| Hypromellose, 5cP | 2.0 mg | 4.1 mg |

Tolterodine L-Tartrate IR Tablets 2 mg

Commercially available tolterodine L-tartate 2 mg tablets for immediate release (IR) (Detrusitol®, Pharmacia & Upjohn AB, Sweden) were used. The tablets had the following composition:

| Core | |
| --- | --- |
| Tolterodine L-tartrate | 2.0 mg |
| cellulose, microcrystalline | 53.4 mg |
| calcium hydrogen phosphate dihydrate | 18.0 mg |
| sodium starch glycollate | 6.0 mg |
| magnesium stearate | 0.4 mg |
| colloidal anhydrous silica | 0.2 mg |
| Coating | |
| Methylhydroxypropyl cellulose | 1.5 mg |
| cellulose, microcrystalline | 0.3 mg |
| stearic acid | 0.6 mg |
| titanium dioxide E 171 | 0.6 mg |

PHARMACODYNAMIC AND PHARMACOKINETIC STUDIES

A clinical trial was performed in patients with overactive bladder to determine the pharmacodynamic and pharmacokinetic effects of different daily doses of (i) the above described tolterodine controlled release capsule (below referred to as TOD), compared with (ii) the above described tolterodine immediate release tablet (below referred to as TIR), and (iii) a placebo capsule (containing sugar spheres only). The trial was performed as a double-blind, double dummy, cross-over trial in 60 patients for three one week periods and six treatments (2, 4, 6 and 8 mg TOD once daily, 2 mg TIR twice daily, and placebo). All patients were randomised to three out of six treatments, meaning that 30 patients were subjected to each of the treatments. Pharmacodynamic and pharmacokinetic measurements were performed on day seven in each treatment period. The determinations included measurements of (i) serum concentrations of tolterodine and its main 5-hydroxymethyl metabolite (below called 5-HM) over time, (ii) salivation (dry mouth), and (iii) residual urine volumes.

Serum Concentrations of Tolterodine and Main Metabolite

Blood samples were drawn immediately before dosing and after 0.5, 1, 2, 3, 6, 9, 12, 24 and 25 hours, and the free (unbound) serum concentrations of tolterodine and its 5-HM metabolite were measured by gas chromatography/mass spectrometry. The unbound concentrations were calculated assuming a fraction unbound of 3.7% for tolterodine and of 36% for 5-HM as obtained from protein binding studies on human serum (Nilvebrant, L., et al., Life Sciences, Vol. 60, Nos. 13/14 (1997) 1129–1136). FIG. 1 shows the obtained variation with time of the sum of the unbound concentrations of tolterodine and 5-HM (which sum is referred to as "active moiety") for, on the one hand, the administration of a 4 mg TOD capsule once daily, and, on the other hand, the administration of a 2 mg TIR tablet twice daily (i.e. equivalent 24-hour doses of capsule and tablet). As shown in the Figure, the peaks obtained with the TIR tablet are eliminated with the TOD capsule, the latter thus providing a substantially constant serum concentration of active moiety during the 24 hours illustrated.

The difference in fluctuation of the serum concentrations between TIR tablet and TOD capsule may also be demonstrated by calculation of the "fluctuation index". The fluctuation index, FI, is calculated as $FI=(Cmax-Cmin)/AUC\tau/\tau$, where $\tau$ is the length of the dosage interval and $AUC\tau$ is the area under the serum concentration profile during a dosage interval. Thus, the mean calculated fluctuation index for the active moiety was 2.40 (95% CI 1.95–2.63) for the TIR tablet (based on n=28), and 0.68 (95% CI 0.59–0.78) for the TOD capsule.

Salivation (Dry Mouth)

Salivation was measured using dental cotton rolls applied in the mouth for 3×2 minutes. Measurements were performed before breakfast and thereafter after each blood sample on day seven in each treatment period. Based on all measurements after dosing, the mean salivation during 12 hours was calculated. The basal salivation at steady state was measured after treatment with (i) 4 mg TOD capsule, (ii) 2 mg TIR tablet, and (iii) placebo. The results are presented in FIG. 2. As can be seen in the Figure, the salivation is substantially constant during the period shown for the TOD capsule, whereas a considerable reduction in salivation (i.e. drier mouth) is obtained with the TIR tablet.

Figure 2:
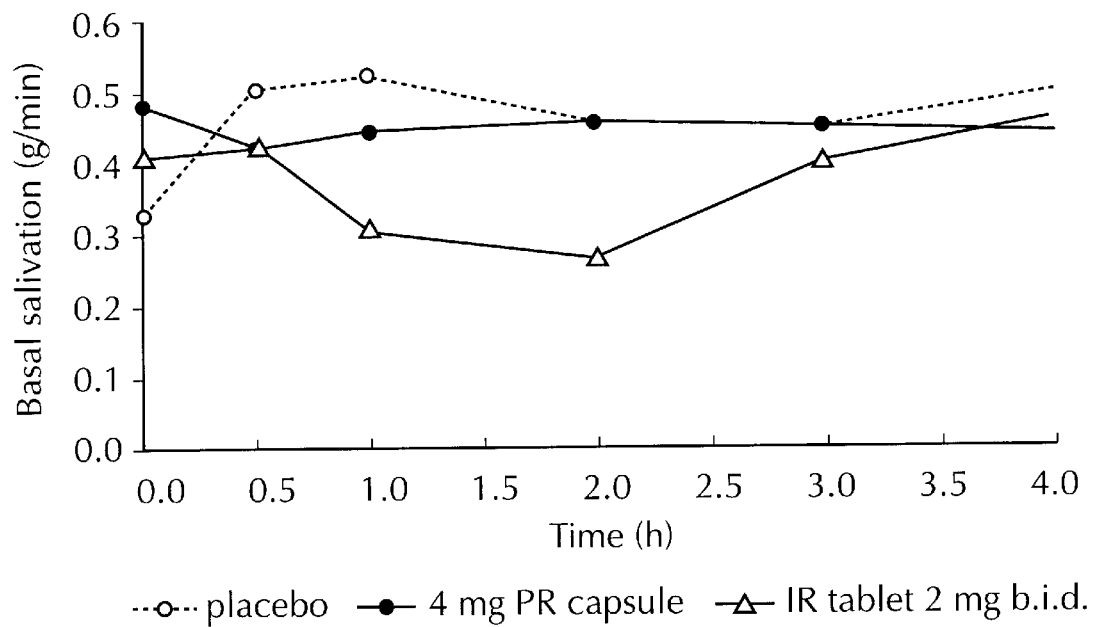
FIG. 2 is a diagram showing the variation of the basal salivation (9/min) with time (hours) during 4 hours after administration of (i) a 4 mg tolterodine controlled release capsule in accordance with the present invention, (ii) a prior art tolterodine immediate release tablet, and (iii) placebo.
Figure 3:
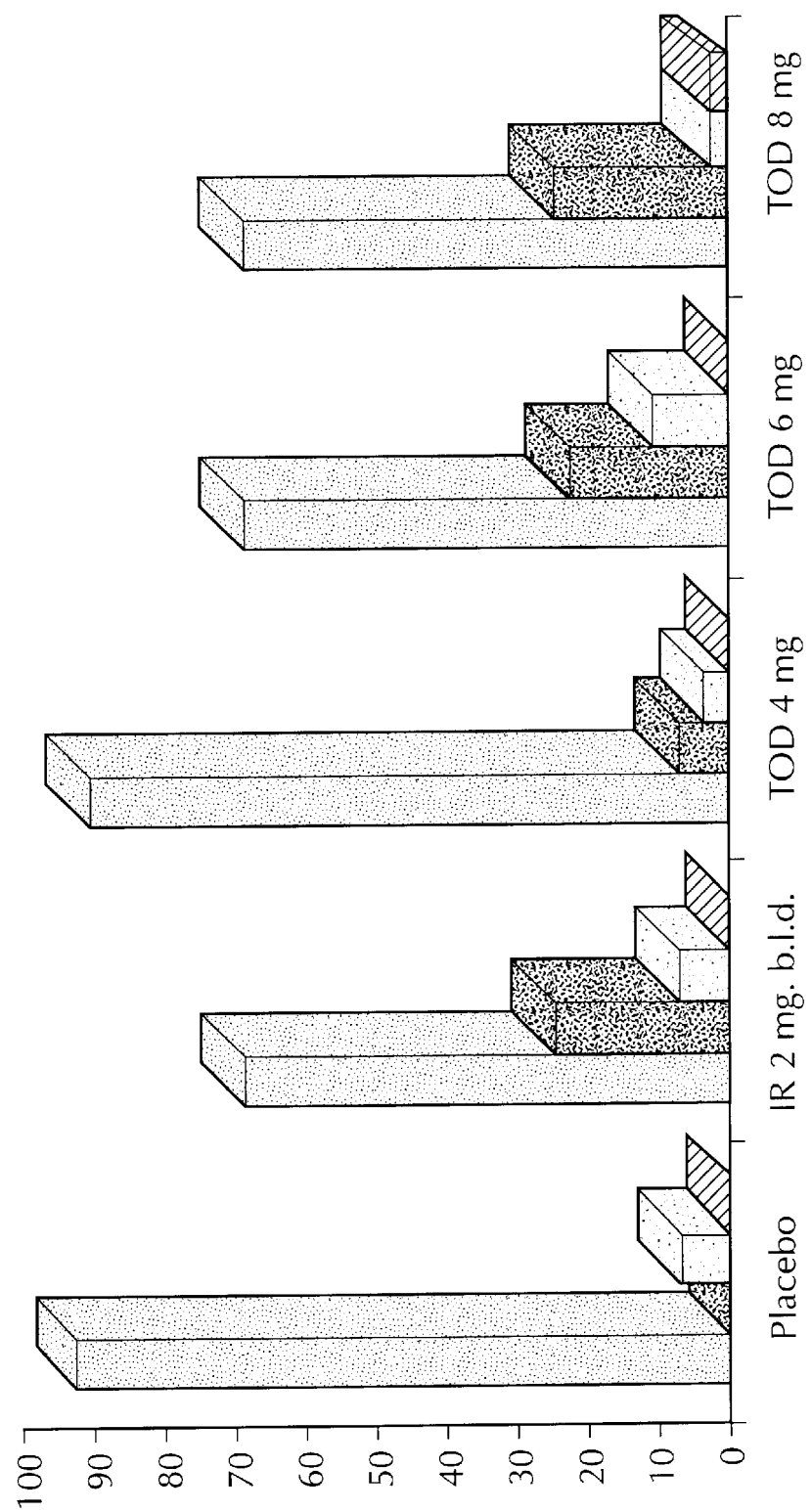
FIG. 3 is is a bar chart diagram showing patients' individual estimates of experienced dry mouth side effect (no dry mouth, mild, moderate, severe) after administration of tolterodine through (i) a conventional 2 mg immediate release tablet, (ii) controlled release capsules of 4, 6 and 8 mg, respectively, according to the present invention, and (iii) placebo.

While FIG. 2 shows the total salivation as measured, the degree of salivation, or dry mouth, was also determined, based on the patient's estimate of experienced intensity of the phenomenon. The results for 2 mg TIR tablet b.i.d., 4 mg TOD capsule, 6 mg TOD capsule and 8 mg TOD capsule, are presented in bar chart form in FIG. 3. The four bars for each dosage represent, from left to right in the figure, no dry mouth, mild, moderate, and severe, respectively.

As apparent from FIG. 2, the dry mouth intensity for the TIR 2 mg b.i.d. tablet is clearly higher than that of the TOD 4 mg capsule, and about twice that dosage, i.e. TOD 8 mg, is required to match the adverse dry mouth effects of the TIR 2 mg b.i.d. tablet.

The results from the salivation determinations thus show that flattening of the concentration peaks of the "active moiety" (i.e. tolterodine plus 5-HM) leads to a substantial reduction of the undesired dry mouth effect.

Residual Urine Volume

Residual volume is the volume of urine left in the bladder immediately after voiding. Measuring residual volume offers a method of assessing the effect of antimuscarinic treatment on the bladder. In fact, it offers a measure of efficacy (change in residual volume) as well as safety (urinary retention, i.e. inability to pass urine). Efficacy may thus be measured as the mean residual volume per unit of time, and safety as any case where the residual urine exceeds a fixed level. The mean residual volume per micturition was measured by a non-invasive (ultrasonic) method for placebo, TIR tablet 2 mg b.i.d., and for capsules TOD 2 mg, TOD 4 mg, TOD 6 mg, and TOD 8 mg.

The results are presented in Tables 1 and 2 below. Table 1 shows the mean residual volume per micturition, and Table 2 shows the maximum residual volume during 12 hours.

The results presented clearly demonstrate that the TOD capsule dosages are as efficacious as the corresponding TIR b.i.d dosages, and also that the TOD dose may be increased up to 8 mg daily and still be safe with regard to urinary retention.

TABLE 1

Mean Residual Volume per micturition (ml)

|  | Placebo | TIR 2 mg b.i.d | TOD 2 mg | TOD 4 mg | TOD 6 mg | TOD 8 mg |
| --- | --- | --- | --- | --- | --- | --- |
| Estimated mean | 29 | 62 | 40 | 59 | 69 | 77 |
| 95% confidence interval | 12 to 46 | 45 to 79 | 26 to 55 | 51 to 66 | 60 to 78 | 65 to 89 |
| Estimated difference vs. IR |  |  | −22 | −4 | 7 | 14 |
|  |  |  | −44 to 1 | −23 to 15 | −13 to 26 | −7 to 36 |

TABLE 2

Maximum Residual Volume during 12 hours

|  | Placebo | TIR 2 mg b.i.d | TOD 2 mg | TOD 4 mg | TOD 6 mg | TOD 8 mg |
| --- | --- | --- | --- | --- | --- | --- |
| Median value (ml) | 46 | 72 | 45 | 55 | 87 | 77 |
| min–max | 5–267 | 10–316 | 0–192 | 0–349 | 0–360 | 0–390 |

The results from the clinical trial described above demonstrate that a flatter serum concentration of active moiety (tolterodine plus 5-HM) not only does not lead to a loss of efficacy or to untoward side-effects, primarily urinary retention, but, importantly, also provides for a reduced dry mouth effect (unaffected or less reduced salivation).

EXAMPLE 2

TOLTERODINE TRANSDERMAL PATCH FORMULATION

Tolterodine-releasing patches were prepared as follows:
System 1 (Drug-in-Adhesive, Acrylate)

5 g of tolterodine base were dissolved in 11 g of ethanol and added to 20 g of Durotak 387-2287 (National Starch & Chemical, U.S.A.). The drug gel was coated onto a backing membrane (Scotchpak 1012; 3M Corp., U.S.A.) by using a coating equipment (RK Print Coat Instr. Ltd, Type KCC 202 control coater). The wet layer thickness was 400 μm. The laminate was dried for 20 min. at RT and then for 30 min. at 40° C. A polyester release liner (S 2016; Rexam Release) was laminated onto the dried drug gel. The sheet was cut into patches and stored at 2–8° C. until use (packed in Barex pouches). The concentration of tolterodine base in the patches was 2,5 mg/cm².
System 2 (Multi-laminate, Acrylate)

5 g of tolterodine base were dissolved in 10 ml of ethanol. A mix of 6,4 g of Eudragit RL 100 (Röhm GmbH Chemische Fabrik, Germany) and 6,4 of ethanol and a mix of 2,6 g of Polyvidone 90 (BASF, Germany) and 10,2 g of ethanol were added to the solution of tolterodine base in ethanol. Finally, 4 g of propylene glycol were added. The drug gel was coated onto a backing membrane (Scotchpak 1109; 3M Corp., U.S.A.) by using the coating equipment above. The wet layer thickness was 400 μm. The laminate was then dried at 40° C. for 2 hours. An adhesive layer consisting of Plastoid E35H was coated onto a polyester film (S 2016; Rexam Release) and dried at 80° C. for 10 min. The two layers were thereafter laminated. The sheet was cut into patches and stored at 2–8° C. until use (packed in Barex pouches). The concentration of tolterodine base in the patches was 2,0 mg/cm².
System 3 (Multi-laminate Water-based Acrylate)

1 g of tolterodine base was mixed with Tween 80 (Merck) by heating to 60–70° C. 1,8 g of triethylacetate and 1,3 g of dem. water was added to the mix. The final mix was then added to 25 g of Eudragit RL 30 D (Röhm GmbH Chemische Fabrik, Germany). Finally, 180 mg of 1 N NaOH were added. The drug gel was coated onto a backing membrane (Scotchpak 1109; 3M Corp., U.S.A.) by using the coating equipment. The wet layer thickness was 400 μm. The laminate was dried at 40° C. for 2 hours. An adhesive layer consisting of Plastoid E35H was coated onto a polyester film (S 2016; Rexam Release) and dried at 80° C. for 10 min. The two layers were thereafter laminated. The sheet was cut into patches and stored at 2–8° C. until use (packed in Barex pouches). The concentration of tolterodine base in the patches was 0,5 mg/cm².

What is claimed is:

1. A method of treating unstable or overactive urinary bladder, wherein the method comprises administering to a patient in need of such treatment tolterodine, its 5-hydroxymethyl metabolite or the racemate corresponding to tolterodine, or a pharmaceutically acceptable salt thereof, in a pharmaceutically effective amount thereof through a controlled release formulation capable of maintaining a substantially constant serum level of the active moiety or moieties for at least 24 hours, wherein the 24-hour serum profile, expressed as the AUC of unbound tolterodine and 5-hydroxymethyl metabolite, is from 5 to about 150 nM*h.

2. The method according to claim 1, wherein the controlled release formulation provides a mean fluctuation index of said serum level of active moiety or moieties that is not higher than about 2.0, said fluctuation index, FI, being defined as FI=(Cmax−Cmin)/AUCτ/τ, wherein Cmax and Cmin are the maximum and minimum concentrations, respectively, of active moiety or moieties, AUCτ is the area under the serum concentration profile, and τ is the length of the dosage interval.

3. A method of treating unstable or overactive urinary bladder, wherein the method comprise administering to a patient in need of such treatment tolterodine, its 5-hydroxymethyl metabolite or the racemate corresponding to tolterodine, or a pharmaceutically acceptable salt thereof, in a pharmaceutically effective amount thereof through controlled release formulation capable of maintaining a substantially constant serum level of the active moiety or moieties for at least 24 hours with reduced undesirable side effects and with no reduction in the efficacy of the tolterodine compound, wherein the 24-hour serum profile, expressed as the AUC of unbound tolterodine and 5-hydroxymethyl metabolite, is from 5 to about 150 nM*h.

4. The method according to claim 1, wherein tolterodine, its 5-hydroxymethyl metabolite or the racemate corresponding to tolterodine is administered, and the serum level of unbound tolterodine and 5-hydroxymethyl metabolite is in the range of about 0.2 to about 6.3 nM.

5. The method according to claim 1 wherein the controlled release formulation is a capsule or tablet for oral administration once daily.

6. The method according to claim 1, wherein the controlled release formulation is a transdermal preparation.

7. The method according to claim 1 wherein tolterodine is administered.

8. The method according to claim 1 wherein urinary incontinence is treated.

9. A pharmaceutical formulation containing tolterodine, its 5-hydroxymethyl metabolite or the racemate corresponding to tolterodine, or a pharmaceutically acceptable salt thereof, which formulation when administered to a patient provides controlled release of tolterodine, its 5-hydroxymethyl metabolite or the racemate corresponding to tolterodine, or salt thereof, such that a substantially constant serum level of the active moiety or moieties is maintained for at least 24 hours, wherein the 24-hour serum profile, expressed as the AUC of unbound tolterodine and 5-hydroxymethyl metabolite, is from 5 to about 150 nM*h.

10. The formulation of claim 9, which provides a mean fluctuation index of said serum level of active moiety or moieties that is not higher than about 2.0, said fluctuation index, FI, being defined as FI=(Cmax−Cmin)/AUCτ/τ, wherein Cmax and Cmin are the maximum and minimum concentrations, respectively, of active moiety or moieties, AUCτ is the area under the serum concentration profile, and τ is the length of the dosage interval.

11. A pharmaceutical formulation containing tolterodine, its 5-hydroxymethyl metabolite or the racemate corresponding to tolterodine, or a pharmaceutically acceptable salt thereof, which formulation when administered to a patient provides controlled release of said tolterodine, its 5-hydroxymethyl metabolite or the racemate corresponding to tolterodine, or pharmaceutically acceptable salt thereof, such that a substantially constant serum level of the active moiety or moieties is maintained for at least 24 hours for efficacious therapy with reduced undesirable side effects, wherein the 24-hour serum profile, expressed as the AUC of unbound tolterodine and 5-hydroxymethyl metabolite, is from 5 to about 150 nM*h.

12. The formulation according to claim 9, wherein tolterodine, its 5-hydroxymethyl metabolite or the racemate corresponding to tolterodine is administered, and the serum level of unbound tolterodine and 5-hydroxymethyl metabolite is in the range of about 0.2 to about 6.3 nM.

13. The formulation according to claim 9, which is a capsule or tablet for oral administration once daily.

14. The formulation according to claim 1, which is a transdermal preparation.

15. The formulation according to claim 9, which provides controlled release of tolterodine.

16. The method of claim 3, wherein the controlled release formulation is administered orally.

17. The formulation of claim 11, which is in a form for oral administration.

18. The method according to claim 2, wherein the controlled release formulation provides a mean fluctuation index of said serum level of active moiety or moieties that is not higher than about 1.0.

19. The method according to claim 3, wherein the 24-hour serum profile, expressed as the AUC of unbound tolterodine and 5-hydroxymethyl metabolite, is from about 10 nM*h to about 120 nM*h.

20. The method according to claim 4, wherein the serum level of unbound tolterodine and 5-hydroxymethyl metabolite is in the range of about 0.4 to about 5.0 nM.

21. The method according to claim 6, wherein the transdermal preparation is a transdermal patch.

22. The formulation of claim 10, wherein the mean fluctuation index of said serum level of active moiety or moieties that is not higher than about 1.0.

23. The formulation according to claim 11, wherein the 24-hour serum profile, expressed as the AUC of unbound tolterodine and 5-hydroxymethyl metabolite, is from about 10 nM*h to about 120 nM*h.

24. The formulation according to claim 12, wherein the serum level of unbound tolterodine and 5-hydroxymethyl metabolite is in the range of about 0.4 to about 5.0 nM.

25. The transdermal preparation of claim 14, which is a transdermal patch.

26. The method of claim 3, wherein increased efficacy of the tolterodine compound is obtained with minimal undesirable side effects.

27. The formulation of claim 11, wherein increased efficacy of the tolterodine compound is obtained with minimal undesirable side effects.

* * * * *